(12) United States Patent
Chen et al.

(10) Patent No.: US 9,239,324 B2
(45) Date of Patent: Jan. 19, 2016

(54) ANTIBODY-BINDING PROTEIN-DRUG CONJUGATE AND METHODS OF USE

(71) Applicants: Gang Chen, San Diego, CA (US); Zhenwei Miao, San Diego, CA (US)

(72) Inventors: Gang Chen, San Diego, CA (US); Zhenwei Miao, San Diego, CA (US)

(*) Notice: Subject to any disclaimer, the term of this patent is extended or adjusted under 35 U.S.C. 154(b) by 0 days.

(21) Appl. No.: 14/098,746

(22) Filed: Dec. 6, 2013

(65) Prior Publication Data

US 2015/0160192 A1 Jun. 11, 2015

(51) Int. Cl.
*C07K 16/00* (2006.01)
*C07K 16/30* (2006.01)
*C07K 16/42* (2006.01)
*G01N 33/50* (2006.01)
*G01N 33/53* (2006.01)
*G01N 33/574* (2006.01)
*A61K 47/48* (2006.01)

(52) U.S. Cl.
CPC ...... *G01N 33/5011* (2013.01); *A61K 47/48723* (2013.01); *G01N 2500/04* (2013.01); *G01N 2500/10* (2013.01)

(58) Field of Classification Search
CPC ........ C07K 16/00; C07K 16/30; C07K 16/42; G01N 33/50; G01N 33/53; G01N 33/574

USPC ............................ 530/387.1, 391.1; 435/7.23
See application file for complete search history.

(56) References Cited

U.S. PATENT DOCUMENTS

| 2010/0260786 A1* | 10/2010 | Doronina et al. | .......... 424/181.1 |
| 2011/0217321 A1* | 9/2011 | Torgov et al. | .............. 424/178.1 |
| 2012/0301400 A1* | 11/2012 | Williams et al. | ............... 424/9.1 |
| 2014/0113348 A1* | 4/2014 | Williams et al. | .............. 435/188 |

* cited by examiner

*Primary Examiner* — Yan Xiao
(74) *Attorney, Agent, or Firm* — David B. Waller; Patent Success Strategies, LLC

(57) ABSTRACT

The present invention provides compositions and methods for preparing protein drug conjugate and its application to stem cell therapy and treating cancer cells. The composition is an antibody-binding-therapeutic drug conjugate that binds antibodies targeted to cancer or stem cells. The method of using the composition includes the steps of combining an antibody that targets the cancer cells or stem cells with a sample for a time sufficient to allow said antibody to bind the targeted cells present in said sample and adding the antibody-binding-drug conjugate for a time sufficient to allow binding to the antibody bound to the targeted cells. The presence of the drug reduces the number of or eliminates the targeted cancer cells or stem cells. A similar method is disclosed for selecting antibodies that may be effective antibody drug conjugates.

3 Claims, No Drawings

ANTIBODY-BINDING PROTEIN-DRUG CONJUGATE AND METHODS OF USE

CROSS-REFERENCE TO RELATED APPLICATIONS

Not applicable

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

INCORPORATION-BY-REFERENCE OF MATERIAL SUBMITTED ON A COMPACT DISC

Not applicable

TECHNICAL FIELD

The present invention relates to antibody binding agent-drug conjugates (abADC) and methods of using the same for reducing the number or eliminating of target cells. The conjugate comprises an antibody binding agent with high binding affinity for antibodies that target cells of interest such as cancer or stem cells.

BACKGROUND OF THE INVENTION

Monoclonal antibody (mAb) for the treatment of cancer, like AVASTIN™ (anti-VEGF) for colon cancer, RITUXAN™ (Rituximab; anti-CD20) for Non-Hodgkin's Lymphoma and HERCEPTIN™ (anti-Her2) for breast cancer have demonstrated that unconjugated antibodies can improve patient survival without the toxicity experienced with conventional chemotherapy treatments.

Monoclonal antibodies bind to target cells and activate the immune system to eliminate the cell. Increased efficiency can be achieved by conjugating a therapeutic agent to mAbs to form an antibody drug conjugate (ADC). ADCs deliver the therapeutic agent directly to the cell without the need for activating the immune response system. The linkage of the antibody to the drug can be direct, or indirect via a linker. One of components believed to be important for developing effective and well-tolerated ADCs is the composition and stability of the linker. For some types of ADCs, the linker desirably provides serum stability, yet selectively releases the drug at or within the target cell.

Attachment of a linker to a mAb can be accomplished in a variety of ways, such as through surface lysines, reductive-coupling to oxidized carbohydrates, and through cysteine residues liberated by reducing interchain disulfide linkages. A variety of ADC linkage systems have been described in the literature, including hydrazone-, disulfide- and peptide-based linkages. Some hydrazone and disulfide-based linkers can be labile in circulation, resulting in release of drug outside the targeted tissue. It is believed that this premature release of drug might lead to systemic toxicity or organ-specific toxicity and/or less than optimal therapeutic efficacy. Peptide-based linker strategies may provide linkers of higher stability; however, the increased associated hydrophobicity of some linkers may lead to aggregation, particularly with strongly hydrophobic drugs. Such aggregation may lead to non-specific uptake of the ADCs into non-targeted tissues, potentially affecting non-target toxicity.

Consequently, there remains a need for targeted delivery of drugs, resulting in reduction or elimination of targeted cells while reducing toxicity to non-target cells.

These and other limitations and problems of the past are solved by the present invention. The recitation of any reference in this application is not an admission that the reference is prior art to this application.

SUMMARY OF THE INVENTION

The present invention provides a composition comprising one or more therapeutic drugs bound to an antibody-binding agent that binds antibodies targeted to cancer or stem cells.

In one embodiment, the antibody-binding agent is a protein such as protein A, Protein G, Protein A/G or Protein L or a secondary antibody that binds the targeting antibodies.

In another embodiment, the therapeutic drug is selected from the group consisting of a microtubulin binding agent (e.g., mono methyl auristatin E), a DNA interchelating agent and/or an antineoplastic agent. (e.g., doxorubicin)

A number of therapeutic agents may be utilized with the present invention, including radioisotopes, cytostatic and chemotherapeutic agents. Radioisotopes that may be utilized with the present invention include for example, $^{211}$At, $^{131}$I, $^{125}$I, $^{90}$Y, $^{186}$Re, $^{188}$Re, $^{153}$Sm, $^{212}$Bi, $^{32}$P and $^{60}$C, Examples of chemotherapeutic agents include for example, Erlotinib (TARCEVA™, Genentech, Oceanside, Calif.), Bortezomib (VELCADE™, Millenium Pharmaceuticals, Cambridge, Mass.), Fulvestrant (FASLODEX™, AstraZeneca, Wilmington, Del.), Sutent (SU11248, Pfizer, New York, N.Y.), Letrozole (FEMARA™, Novartis, Basal Switzerland), Imatinib mesylate (GLEEVEC™, Novartis, Basal Switzerland), PTK787/ZK 222584 (Novartis, Basal Switzerland), Oxaliplatin (Eloxatin™, Sanofi, Bridgewater, N.J.), Leucovorin, Rapamycin (Sirolimus, RAPAMUNE™, Pfizer New York, N.Y.), Lapatinib (GSK572016, GlaxoSmithKline, Philadelphia, Pa.), Lonafarnib (SCH 66336), Sorafenib (BAY43-9006, Bayer Labs. Leversen, Germany), and Gefitinib (IRESSA™, AstraZeneca, Wilmington, Del.), AG1478, AG1571 (SU 5271; Sugen), alkylating agents such as thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (Angew Chem Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™ paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluoromethylornithine (DMFO); and retinoids such as retinoic acid; capecitabine. Other therapeutic agents include antibodies such as anti-Her2, anti-EGFR, anti-EGFR3, anti-cMET, anti-IGG-1R, anti-ephA2, anti-CD22 anti-CD30, Herceptin™ (Genentech, Oceanside, Calif.), Erbitux™ (Eli Lilly and Company, New York, N.Y. and Bristol-Myers Squibb Company, Princeton, N.J.) and Rituxan™ (Biogen-Idec, San Diego, Calif. and Genentech, Oceanside, Calif.).

In still another embodiment, a variety of antibodies may be utilized with the present invention. Some exemplary parent antibodies include for example, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD44 antibody, anti-CD51 antibody, anti-CD71 antibody, anti-CD100 anti-CD117 antibody, anti-CD95/Fas antibody, anti-CD99 antibody, anti-CD106 antibody, anti-CD71 antibody, anti-c-myc antibody, anti-cytokeratins antibody, anti-vimentins antibody, anti-melanosomes antibody, and anti-prostate specific antigen antibody.

In yet another embodiment, a variety of cancer cells may be treated with the compositions of the present invention. Examples of the types of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, as well as head and neck cancer. As an example but not by way of limitation cell lines obtained from any of these cancers may be treated with the compositions of the present invention. For example, cell lines of breast cancer include the cell lines, SKBR3, MDA-MB-453, MCF-7, T47D, SUM185, BT474, ZR-75, MDA-MB-468, SUM190, BT549, and MDA-MB-231.

In still another embodiment, the compositions of the present invention may be utilized with a variety of stem cell therapy treatments including those that target bone marrow, adipose tissue, blood, umbilical cord blood, embryonic stem cells; induced pluripotent stem cells.

Another aspect of the present invention is a method of reducing or eliminating cancer cells or stem cells comprising the steps of combining an antibody with a sample for a time sufficient to allow the antibody to bind the targeted cancer or stem cells that may be present in the sample. Then adding an abADC for a time sufficient to allow the conjugate to bind the antibody bound to the targeted cells wherein the presence of the therapeutic drug reduces the number of or eliminates the targeted cells.

Yet another aspect of the present invention is a method of identifying antibodies as effective antibody-drug conjugates. The method comprises the steps of combining an antibody with target cells for a time sufficient to allow said antibody to bind said target cells. Then adding an antibody-binding agent-drug conjugate containing an antibody binding agent to which one or more therapeutic drug compounds are bound for a time sufficient to allow the conjugate to bind the antibody bound to the target cells. When bound the therapeutic drug compounds are brought into close proximity to the target cell thereby reducing the number of or eliminating said cells. The extent of this reduction or elimination of cells identifies antibodies that may be utilized as effective antibody-drug conjugates.

DESCRIPTION OF THE FIGURES

Not applicable

DETAILED DESCRIPTION

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "antibody binding agent" refers to an agent that binds the targeting antibody with moderate to high affinity. An antibody binding agent may be a secondary antibody that binds the targeting antibody, an antibody that binds to a particular peptide tag that is bound to the targeting antibody, an antibody binding protein, or an aptamer. An "aptamer" as used herein refers to a nucleic acid (e.g., oligonucleic acid) or peptide. In the case of a nucleic acid the aptamer comprises a sequence that specifically binds a tag provided on the targeting antibody. In the case of a peptide, the peptide comprises a amino acid sequence that provides a conformational structure to specifically bind a region of, or a region provided on, the targeting antibody.

A secondary antibody may bind a region of a particular immunoglobulin molecule or may be prepared to bind to the particular targeting antibody being utilized. Binding proteins that bind specifically to immunoglobulins are known in the art and include for example, Protein A, Protein G, Protein A/G and Protein L. In some embodiments, the targeting antibody is labeled with a tag that is recognized by an antibody that is utilized as the binding agent in the abADC. In the case of a nucleotide or oligonucleotide, a sequence is selected to avoid non-specific binding to other nucleotide sequences present in the sample or system that is substantially or completely complimentary to the tag, and is of a length that provides moderate to high binding affinity with the tag. In the case of a peptide, a sequence is selected having a conformational (e.g., tertiary) structure that binds with moderate or high affinity to the tag bound to the targeting antibody.

The term "antibody" as used herein refers to intact monoclonal antibodies, polyclonal antibodies, multispecific antibodies (e.g., bispecific antibodies), and to antibody fragments that exhibit the desired biological activity (e.g., antigen binding). The antibody can be of any type or class (e.g., IgG, IgE, IgM, IgD, and IgA) or sub-class (e.g., IgG1, IgG2, IgG3, IgG4, IgA1 and IgA2).

An "intact" antibody as used herein refers to an antibody that comprises an antigen-binding variable region as well as a light chain constant domain ($C_L$) and heavy chain constant domains, $C_{H1}$, $C_{H2}$, $C_{H3}$, and/or $C_{H4}$, as appropriate for the antibody class. The constant domains may be native sequence constant domains (e.g., human native sequence constant domains) or amino acid sequence variant thereof.

An antibody may have one or more "effector functions" which refer to those biological activities attributable to the Fc region of an antibody. Examples of antibody effector functions include Protein A, G, A/G or L binding; C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR).

The term "single-chain Fv" or "scFv" as used herein refer to antibody fragments that comprise the $V_H$ and $V_L$ domains of an antibody wherein these domains are present in a single polypeptide chain. The Fv polypeptide typically further comprises a polypeptide linker between the $V_H$ and $V_L$ domains which enables the scFv to form the desired structure for antigen binding (see Pluckthun in *The Pharmacology of Monoclonal Antibodies*, vol. 113, Rosenberg and Moore, eds., Springer-Verlag, New York, pp. 269-315 (1994)).

The term "Fab" or "F(ab)2" as used herein refer to antibody fragments that comprise the variable region, the light chain constant region and the $C_{H1}$ domain of the heavy chain. The F(ab)2 antibody fragments can be produced by pepsin digestion of the antibody molecule. Further reduction of the disulfide bridges of the F(ab)2 fragments results in the production of Fab fragments.

The term "diabody" or "diabodies" as used herein refers to an antibody fragment comprising a heavy (VH) chain variable domain connected to a light chain variable domain (VL) on the same polypeptide chain (VH-VL) connected by a peptide linker that is too short to allow pairing between the two domains on the same chain. This forces paring with the complementary domains of another chain and promotes the assembly of a dimeric molecule with two functional antigen binding sites. Bispecific diabodies may be constructed by fusing the V-domains of antibody A and antibody B to create the two chains VHA-VLB, VHB-VLA. Each chain is inactive in binding to antigen, but recreates the functional antigen binding sites of antibodies A and B on pairing with the other chain. Diabodies may be expressed in bacteria (*E. coli*) and yeast (*Pichia pastoris*) in functional form and in high yields.

An "isolated" antibody as used herein refers to an antibody that has been identified and separated and/or recovered from a component of its natural environment. In some embodiments, the antibody is isolated by at least one purification step and purified (1) to greater than 95% by weight of antibody as determined by the Lowry method, or greater than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or silver stain.

An antibody "which binds" an antigen of interest is one capable of binding that antigen with sufficient affinity such that the antibody is useful in targeting a cell expressing the antigen.

The terms "specifically binds" and "specific binding" as used herein refer to antibody binding to a predetermined antigen. Typically, the antibody binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen.

The term "therapeutically effective amount" as used herein refers to an amount of a drug (e.g., a protein drug conjugate) effective to treat a disease or disorder in an animal. In the case of cancer, the therapeutically effective amount of the drug may reduce the number of cancer cells; reduce the tumor size; interfere with (i.e., slow to some extent and preferably stop) cancer cell infiltration into peripheral organs; interfere with (i.e., slow to some extent and preferably stop) tumor metastasis; inhibit to some extent, tumor growth and/or proliferation; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

In the case of stem cells, the therapeutically effective amount of the drug reduces the number of or eliminates stem cells and/or interferes with or prevents proliferation of stem cells.

The terms "target polypeptide," "target protein" and "target antigen" as used herein refer to a protein, polypeptide, and in addition in the case of a "target antigen," another molecule on the surface of or associated with a target cell.

The phrase "pharmaceutically acceptable salt" as used herein refers to a pharmaceutically acceptable organic or inorganic salt of a protein drug conjugate and/or its associated antibody that binds the target cell. The conjugate may contain at least one amino group, and accordingly acid addition salts can be formed with the amino group. Exemplary salts include, but are not limited, to acetate, ascorbate, benzenesulfonate, benzoate, bisulfate, bitartrate, citrate, ethanesulfonate, formate, fumarate, gentisinate, gluconate, glucuronate, glutamate, isonicotinate, lactate, maleate, methanesulfonate, nitrate, oleate, oxalate, pamoate (i.e., 1,1' methylene bis-(2 hydroxy 3 naphthoate), pantothenate, phosphate, p-toluenesulfonate, saccharate, salicylate, succinate, sulfate, tannate, tartrate, chloride, bromide, iodide, acid citrate and acid phosphate salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ions.

The phrases "pharmaceutically acceptable solvate" or "solvate" as used herein refer to an association of one or more solvent molecules and a protein drug conjugate and/or its associated antibody that binds the target cell. Examples of solvents that form pharmaceutically acceptable solvates include, but are not limited to, water, isopropanol, ethanol, methanol, DMSO, ethyl acetate, acetic acid, and ethanolamine.

The terms "patient" or "subject" include, as used herein refer to but are not limited to, a human, rat, mouse, guinea pig, monkey, pig, goat, cow, horse, dog, cat, bird and fowl. In an exemplary embodiment, the patient or subject is a human.

The term "sample" as used herein refers to ascites fluid produced in a mouse, recombinant antibody IgG from a mammalian cell line (e.g., 293 or CHO), or a solution containing scFV, diabody, and Fab expresses in a cell line (e.g., E. coli or yeast), or expressed in an in vitro expression system (e.g., expression systems such as those sold by Sutro Biopharma, Inc. San Francisco, Calif. or Ambrx, Inc., San Diego, Calif.)

The terms "treat" or "treatment," as used herein, unless otherwise indicated by context, refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, elimination or reduction in the number of target cells, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

In the context of cancer, the term "treating" includes any or all of: preventing growth of tumor cells, cancer cells, or of a tumor; preventing replication of tumor cells or cancer cells, lessening of overall tumor burden or decreasing the number of cancerous cells, and ameliorating one or more symptoms associated with the disease.

In the context of stem cells, the term "treating" includes reducing the number of or eliminating stem cells and/or interfering with or preventing differentiation of stem cells (e.g., bone marrow stem cells or induced pluripotent (iPS) derived stem cells.

1.0 the Ligand Unit

The Ligand unit includes within its scope any unit of a Ligand that binds or reactively associates or complexes with a receptor, antigen or other receptive moiety associated with a given target-cell population. A Ligand can be any molecule that binds to, complexes with or reacts with a moiety of a cell population sought to be therapeutically or otherwise biologically modified. The Ligand unit acts by binding the target cell and which is bound by the protein drug conjugate to deliver the Drug unit to the particular target cell population with which the Ligand unit reacts. Such Ligands include, but are not limited to, large molecular weight proteins such as, for example, full-length antibodies, antibody fragments, and smaller molecular weight proteins, polypeptides or peptides.

1.1 Polyclonal Antibodies

Useful polyclonal antibody Ligands are heterogeneous populations of antibody molecules derived from the sera of immunized animals. Various procedures well known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, and guinea pigs. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as Bacille Calmette-Guerin (BCG) and *Corynebacterium parvum*. Such adjuvants are also well known in the art.

1.2 Monoclonal Antibodies

Useful mAb Ligands are homogeneous populations of antibodies to a particular antigen (e.g., a cancer cell antigen, a stem cell antigen, or the like). A mAb to an antigen-of-interest can be prepared by using any technique known in the art which provides for the production of antibody molecules by continuous cell lines in culture. These include, but are not limited to, the hybridoma technique originally described by Kohler and Milstein (Nature 256:495497 (1975)), the human-B cell hybridoma technique (Kozbor et al., Immunology Today 4:72 (1983)), and the EBV-hybridoma technique (Cole et al., Monoclonal Antibodies and Cancer Therapy, Alan R. Liss, Inc., pp. 77-(1985)). Such antibodies may be of any immunoglobulin class including IgG, IgM, IgE, IgA, and IgD and any subclass thereof. The hybridoma producing the mAbs of use in this invention may be cultivated in vitro or in vivo.

Useful mAb Ligands include, but are not limited to, human mAbs or chimeric human-mouse (or other species) mAs. Human mAbs may be made by any of numerous techniques known in the art (e.g., Teng et al., Proc. Natl. Acad. Sci. U.S.A. 80:7308-7312 (1983); Kozbor et al., Immunology Today 4, 72-79 (1983); and Olsson et al., Meth. Enzymol. 92:3-16 (1982)).

1.3 Bispecific Antibodies

The Ligand can also be a bispecific antibody. Methods for making bispecific antibodies are known in the art. Traditional production of full-length bispecific antibodies is based on the coexpression of two immunoglobulin heavy chain-light chain pairs, where the two chains have different specificities (Milstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually performed using affinity chromatography steps, is rather cumbersome, and the product yields are low. Similar procedures are disclosed in WO 93/08829, and in Traunecker et al., EMBO J. 10:3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690) which is incorporated herein by reference in its entirety.

For further details for generating bispecific antibodies see, for example, Suresh et al., Methods in Enzymology, 1986, 121:210. Using such techniques, bispecific antibody Ligands can be prepared for use in the treatment or prevention of disease as defined herein.

Bifunctional antibodies are also described, in EPO 105, 360. As disclosed in this reference, hybrid or bifunctional antibodies can be derived either biologically, (i.e., by cell fusion techniques) or chemically, especially with cross-linking agents or disulfide-bridge forming reagents, and may comprise whole antibodies or fragments thereof. Methods for obtaining such hybrid antibodies are disclosed for example, in WO 83/03679, and EPO 217,577, both of which are incorporated herein by reference.

1.4 Recombinant Antibodies

Additionally, recombinant antibodies, such as chimeric and humanized monoclonal antibodies, comprising both human and non-human portions, which can be made using standard recombinant DNA techniques, are useful Ligands. A chimeric antibody is a molecule in which different portions are derived from different animal species, such as those having a variable region derived from a murine monoclonal and a human immunoglobulin constant region (see, e.g., Cabilly et al., U.S. Pat. No. 4,816,567; and Boss et al., U.S. Pat. No. 4,816,397, which are incorporated herein by reference in their entirety). Humanized antibodies are antibody molecules from non-human species having one or more complementarity determining regions (CDRs) from the non-human species and a framework region from a human immunoglobulin molecule (e.g., U.S. Pat. No. 5,585,089, incorporated herein by reference in its entirety). Such chimeric and humanized monoclonal antibodies can be produced by recombinant DNA techniques known in the art, for example using methods described in International Publication No. WO 87/02671; EPO 184, 187; EPO 171,496; EPO 173,494; WO 86/01533; U.S. Pat. No. 4,816,567; EPO 125,023; Berter et al., 1988, Science 240:1041-1043; Liu et al., Proc. Natl. Acad. Sci. USA 84:3439-3443 (1987); Liu et al., J. Immunol. 139:3521-3526 (1987); Sun et al., Proc. Natl. Acad. Sci. USA 84:214-218 (1987); Nishimura et al., Canc. Res. 47:999-1005 (1987); Wood et al., Nature 314:446-449 (1985); and Shaw et al., J. Natl. Cancer Inst. 80:1553-1559 (1988); Morrison, Science 229:1202-1207 (1985); Oi et al., BioTechniques 4:214 (1986); U.S. Pat. No. 5,225,539; Jones et al., Nature 321:552-525 (1986); Verhoeyan et al., Science 239:1534 (1998); and Beidler et al., J. Immunol. 141:4053-4060 (1988); each of which is incorporated herein by reference in its entirety.

Completely human antibodies are particularly desirable for Ligands. Such antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (Int. Rev. Immunol. 13:65-93 (1995)). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806; each of which is incorporated herein by reference in its entirety. Other human antibodies can be obtained commercially from, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody (e.g., a mouse antibody) is used to guide the selection of a completely human antibody recognizing the same epitope (Jespers et al., Biotechnology 12:899-903 (1994)).

In a specific embodiment, known antibodies for the treatment or prevention of cancer are used in accordance with the compositions and methods of the invention. Antibodies immunospecific for a cancer cell antigen can be obtained commercially or produced by any method known to one of skill in the art such as, for example, chemical synthesis or recombinant expression techniques.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE 4 (carcinomas), anti-transferrin receptor (carcinomas), p97 (melanoma), MUC1-KLH (breast cancer), CEA (colorectal), gp100 (melanoma), MARTI (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific useful antibodies include, but are not limited to, BR96 mAb (Trail, P. A., Willner, D., Lasch, S. J., Henderson, A. J., Hofstead, S. J., Casazza, A. M., Firestone, R. A., Hellstrom, I., Hellstrom, K. E., "Cure of Xenografted Human Carcinomas by BR96-Doxorubicin Immunoconjugates" Science 261:212-215 (1993)), BR64 (Trail, Pa., Willner, D, Knipe, J., Henderson, A. J., Lasch, S. J., Zoeckler, M. E., Trailsmith, M. D., Doyle, T. W., King, H. D., Casazza, A. M., Braslawsky, G. R., Brown, J. P., Hofstead, S. J., (Greenfield, I L S., Firestone, R. A., Mosure, K., Kadow, D. F., Yang, M. B., Hellstrom, K E., and Hellstrom, I. "Effect of Linker Variation on the Stability, Potency, and Efficacy of Carcinomareactive BR64-Doxorubicin Immunoconjugates" Cancer Research 57:100-105 (1997), mAbs against the CD40 antigen, such as S2C6 mAb (Francisco, J. A., Donaldson, K. L., Chace, D., Siegall, C. B., and Wahl, A. F. "Agonistic properties and in vivo antitumor activity of the anti-CD-40 antibody, SGN-14" Cancer Res. 60:3225-3231 (2000)), mAbs against the CD70 antigen, such as 1F6 mAb, and mAbs against the CD30 antigen, such as AC10 (Bowen, M. A., Olsen, K. J., Cheng, L., Avila, D., and Podack, E. R. "Functional effects of CD30 on a large granular lymphoma cell line YT" J. Immunol., 151:5896-5906, (1993)). Many other internalizing antibodies that bind to tumor associated antigens can be used in this invention, and have been reviewed (Franke, A. E., Sievers, E. L., and Scheinberg, D. A., "Cell surface receptor-targeted therapy of acute myeloid leukemia: a review" Cancer Biother Radiopharm. 15:459-76 (2000); Murray, J. L., "Monoclonal antibody treatment of solid tumors: a coming of age" Semin Oncol. 27:64-70 (2000); Breitling, F., and Dubel, S., Recombinant Antibodies, John Wiley, and Sons, New York (1998)).

The antibodies suitable for use in the invention can be produced by any method known in the art for the synthesis of antibodies, in particular, by chemical synthesis or by recombinant expression, and are preferably produced by recombinant expression techniques.

2.0 Production of Recombinant Antibodies

Ligand antibodies of the invention can be produced using any method known in the art to be useful for the synthesis of antibodies, in particular, by chemical synthesis or by recombinant expression, and are preferably produced by recombinant expression techniques.

2.1 Obtaining or Generating the Nucleotide Sequence of an Antibody

Recombinant expression of the Ligand antibodies, or fragment, derivative or analog thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., BioTechniques 17:242 (1994)), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody can be generated from a suitable source. If a clone containing the nucleic acid encoding the particular antibody is not available, but the sequence of the antibody is known, a nucleic acid encoding the antibody can be obtained from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

If an antibody that specifically recognizes a particular antigen is not commercially available (or a source for a cDNA library for cloning a nucleic acid encoding such an immunoglobulin), antibodies specific for a particular antigen can be generated by any method known in the art, for example, by immunizing an animal, such as a rabbit, to generate polyclonal antibodies or, more preferably, by generating monoclonal antibodies, e.g., as described by Kohler and Milstein (Nature 256:495-497 (1975)) or, as described by Kozbor et al. (Immunology Today 4:72 (1983)) or Cole et al. (Monoclonal Antibodies and Cancer Therapy, Alan R. Liss, Inc., pp. 77-96 (1985)). Alternatively, a clone encoding at least the Fab portion of the antibody can be obtained by screening Fab expression libraries (e.g., as described in Huse et al., 1989, Science 246:1275-1281) for clones of Fab fragments that bind the specific antigen or by screening antibody libraries (See, e.g., Clackson et al., Nature 352:624 (1991); Hane et al., Proc. Natl. Acad. Sci. USA 94:4937 (1997)).

2.2 Recombinant Antibody Expression Vectors

Once a nucleic acid sequence encoding at least the variable domain of the antibody is obtained, it can be introduced into a vector containing the nucleotide sequence encoding the constant regions of the antibody (see, e.g., International Publication No. WO 86/05807; WO 89/01036; and U.S. Pat. No. 5,122,464). Vectors containing the complete light or heavy chain that allow for the expression of a complete antibody molecule are available. Then, the nucleic acid encoding the antibody can be used to introduce the nucleotide substitutions or deletion necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis and in vitro site directed mutagenesis (Hutchinson et al., J. Biol. Chem. 253:6551 (1978)).

In addition, techniques developed for the production of "chimeric antibodies" (Morrison et al., 1984, Proc. Natl. Acad. Sci. 81:851-855; Neuberger et al., 1984, Nature 312: 604-608; Takeda et al., 1985, Nature 314:452-454) by splicing genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region (e.g., humanized antibodies).

An expression vector comprising the nucleotide sequence of an antibody or the nucleotide sequence of an antibody can be transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

2.3 Host Cells

The host cells used to express the recombinant Ligand antibody can be either bacterial cells such as *Escherichia coli* or, preferably, eukaryotic cells, especially for the expression of whole recombinant immunoglobulin molecule. In particular, mammalian cells (e.g., Chinese hamster ovary cells (CHO)), in conjunction with a vector such as the major intermediate early gene promoter element from human cytomegalovirus is an effective expression system for immunoglobulins (Foecking et al., Gene 45:101 (1980); Cockett et al., BioTechnology 8:2 (1990)).

A variety of host-expression vector systems can be utilized to express the immunoglobulin Ligands. Such host-expression systems represent vehicles by which the coding sequences of the antibody can be produced and subsequently purified, but also represent cells that can, when transformed or transfected with the appropriate nucleotide coding sequences, express a Ligand immunoglobulin molecule in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces Pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

2.31 Bacterial Host Cells

In bacterial systems, a number of expression vectors can be advantageously selected depending upon the use intended for the antibody being expressed. For example, when a large quantity of such a protein is to be produced, vectors that direct the expression of high levels of fusion protein products that are readily purified might be desirable. Such vectors include, but are not limited to, the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors can also be used to express foreign polypeptides as fusion proteins with glutathione 5-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

2.32 Insect Host Cells

In an insect system, *Autographa californica* nuclear polyhedrosis virus (AcNPV) or the analogous virus from *Drosophila Melanogaster* is used as a vector to express foreign genes. The virus grows in *Spodoptera frugiperda* cells. The antibody coding sequence can be cloned individually into non-essential regions (e.g., the polyhedrin gene) of the virus and placed under control of an AcNPV promoter (e.g., the polyhedrin promoter).

2.33 Mammalian Host Cells

In mammalian host cells, a number of viral-based expression systems can be utilized. In cases where an adenovirus is used as an expression vector, the antibody coding sequence of interest can be ligated to an adenovirus transcription/translation control complex (e.g., the late promoter and tripartite leader sequence). This chimeric gene can then be inserted in the adenovirus genome by in vitro or in vivo recombination. Insertion in a non-essential region of the viral genome (e.g., region E1 or E3) results in a recombinant virus that is viable and capable of expressing the immunoglobulin molecule in infected hosts. (e.g., see Logan & Shenk, Proc. Natl. Acad. Sci. USA 81:355-359 (1984)). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., Methods in Enzymol. 153:51-544 (1987)).

In addition, a host cell strain can be chosen to modulate the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERY, BH, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines that stably express an antibody can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method can advantageously be used to engineer cell lines which express the antibody. These engineered cell lines can be particularly useful in screening and evaluation of tumor antigens that interact directly or indirectly with the antibody Ligand.

A number of selection systems can be used, including but not limited to the herpes simplex virus thymidine kinase (tk) (Wigler et al., Cell 11:223 (1977), hypoxanthine-guanine phosphoribosyltransferase (hgprt) (Szybalska & Szybalski, Proc. Natl. Acad. Sci. USA 48:202 (1992)), and adenine phosphoribosyltransferase (aprt) (Lowy et al., Cell 22:817 (1980)) genes can be employed in tk-, hgprt- or aprt-cells, respectively. Also, antimetabolite resistance can be used as the basis of selection for the following genes: dihydorfolate reductase (dhfr), which confers resistance to methotrexate (Wigler et al., Proc. Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIB TECH 11(5):155-215 (1993)) and hygro, which confers resistance to hygromycin (Santerre et al., Gene 30:147 (1984)). Methods commonly known in the art of recombinant DNA technology which can be used are described in Ausubel et al. (eds., Current Protocols in Molecular Biology, John Wiley & Sons, NY; Kriegler (1993), Gene Transfer and Expression, A Laboratory Manual, Stockton Press, NY; and in Chapters 12 and 13 (1990), Dracopoli et al. (eds), Current Protocols in Human Genetics, John Wiley & Sons, NY. (1994); Colberre-Garapin et al., J. Mol. Biol. 150:1 (1981)).

3.0 Antibody Purification

Once the antibody has been recombinantly expressed, it can be purified using any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

4.0 Antibody-Binding Agents

An antibody binding agent may be a secondary antibody, A number of antibody binding proteins is known and may be utilized with the present invention including Protein A, Protein G, Protein A/G and Protein L. Antibody binding protein express high binding affinities for immunoglobulins. For example, Protein A is a 56 kDa surface protein isolated from the cell wall of bacterium *Staphylococcus aureus* and is able to bind the heavy chain within the Fc region of most immunoglobulins. It is composed of five homogeneous Ig-binding domains each able to bind human IgG1 and IgG2 as well as mouse IgG2a and IgG2b with high affinity. It will also bind human IgM, IgA and IgE as well as mouse IgG3 and IgG1 with moderate affinity. Preferably the antibody binding protein is Protein A.

5.0 Preparing Antibody-Binding Agent with Linker

A number of linkers known in the art may be utilized with the present invention. Preferred linkers have binding moieties that allow them to be conjugated to a sulfhydryl group of a protein such as a maleimide moiety or that allow them to be bound via an amine group of the protein such as a succinimidyl moiety. Others moieties such as hydrazines may be used to bind free aldehyde groups of a protein.

A linker that binds a therapeutic drug or that is bound to a therapeutic drug may be bound to an antibody-binding protein though an amino acid unit of the antibody-binding protein or peptide. This bond is usually created through a heteroatom of the protein. Heteroatoms that may be present on the antibody-binding protein or peptide include sulfur (in one embodiment, from a sulfhydryl group), oxygen (in one embodiment, from a carbonyl, carboxyl or hydroxyl group) and nitrogen (in one embodiment, from a primary or secondary amino group). These heteroatoms can be present on the protein in its natural state or can be introduced into the protein via chemical modification.

In a preferred embodiment, the antibody-binding agent has a sulfhydryl group that binds the Linker via the sulfhydryl group's sulfur atom.

In another embodiment, the antibody-binding agent may have one or more carbohydrate groups that can be chemically modified to have one or more sulfhydryl groups.

In yet another embodiment, the antibody-binding agent can have one or more carbohydrate groups that can be oxidized to provide an aldehyde (—CHO) group (see Laguzza, et al., J. Med. Chem., 32(3), 548-55 (1989)). The corresponding aldehyde can form a bond with a reactive site on a linker. Reactive sites on a linker that can react with a carbonyl group on a protein include, but are not limited to, hydrazine and hydroxylamine.

Examples of linkers that may be utilized with the present invention include a divalent radical such as an alkanediyl ($C_nH_{2n}$), an arylene, a heteroarylene, moieties such as —$(CR_2)_nO(CR_2)_n$—, repeating units of alkyloxy (e.g. polyethylenoxy, PEG (e.g., PEG 2 or PEG 4), polymethyleneoxy) and alkylamino (e.g. polyethyleneamino, Jeffamine™); and diacid ester and amides including succinate, succinamide, diglycolate, malonate, and caproamide. As used herein, "arylene" refers to a monocyclic or polycyclic, preferably monocyclic, bivalent aromatic group, preferably having from 5 to about 20 carbon atoms and at least one aromatic ring, more preferably 5 to carbons, even more preferably lower arylene. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a bivalent monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms.

As used herein, "alkyloxy" refers to RO— in which R is alkyl, preferably lower alkyl and "alkylamino" refers to RNH— in which R is alkyl, preferably lower alkyl.

6.0 Partial Reduction of the Binding Protein

In general, to prepare conjugates having 2 drugs per antibody, the relevant antibody is reduced using a reducing agent such as dithiothreitol (DTT) or tricarbonyl ethylphosphine (TCEP) (about 1.8 equivalents) in PBS with 1 mM DTPA, adjusted to pH 8 with 50 mM borate. The solution is incubated at 37° C. for 1 hour, purified using a 50 ml a desalting column (e.g., G25) equilibrated in PBS/1 mM DTPA at 4° C. The thiol concentration can is then determined, the protein concentration can be determined by dividing the $A_{280}$ value by 1.58 extinction coefficient (mg/ml), and the ratio of thiol to antibody can then be determined.

Conjugates having 4 drugs per protein may be made using the same methodology and about 4.2 equivalents of a suitable reducing agent to partially reduce the antibody-binding agent.

7.0 Therapeutic Drugs

A number of therapeutic agents may be utilized with the present invention, including radioisotopes, cytostatic and chemotherapeutic agents. Radioisotopes that may be utilized with the present invention include for example, $^{211}$At, $^{131}$I, $^{125}$I, $^{90}$Y, $^{186}$Re, $^{188}$Re, $^{153}$Sm, $^{212}$Bi, $^{32}$P and $^{60}$C, Examples of chemotherapeutic agents include for example, Erlotinib (TARCEVA™, Genentech, Oceanside, Calif.), Bortezomib (VELCADE™, Millenium Pharmaceuticals, Cambridge, Mass.), Fulvestrant (FASLODEX™, AstraZeneca, Wilmington, Del.), Sutent (SU11248, Pfizer, New York, N.Y.), Letrozole (FEMARA™, Novartis, Basal Switzerland), Imatinib mesylate (GLEEVEC™, Novartis, Basal Switzerland), PTK787/ZK 222584 (Novartis, Basal Switzerland), Oxaliplatin (Eloxatin™, Sanofi, Bridgewater, N.J.), Leucovorin, Rapamycin (Sirolimus, RAPAMUNE™, Pfizer New York, N.Y.), Lapatinib (GSK572016, GlaxoSmithKline, Philadelphia, Pa.), Lonafarnib (SCH 66336), Sorafenib (BAY43-9006, Bayer Labs. Leversen, Germany), and Gefitinib (IRESSA™, AstraZeneca, Wilmington, Del.), AG1478, AG1571 (SU 5271; Sugen), alkylating agents such as thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (Angew Chem Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™ paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluoromethylornithine (DMFO); and retinoids such as retinoic acid; capecitabine. Other therapeutic agents include for example, 2-amino-3-phosphonopropionic acid (AP3), monomethyl auristatin E (MMAE), monmethyl auristatin F (MMAF), amanitin and leptomycin B.

8.0 Conjugation of Drug-Linker to Partially Reduced Antibody-Binding Protein The partially reduced antibody-binding protein samples can be conjugated to a corresponding Drug-Linker compound using about 2.4 and about 4.6 molar equivalents of Drug-Linker compound per protein to prepare the 2 and 4 drug per protein conjugates, respectively. The conjugation reactions are incubated on ice for 1 hour, quenched with about 20-fold excess of cysteine to drug, and purified by elution over a G25 desalting column at about 4° C. The resulting Drug-Linker-Ligand conjugates are concentrated to about 3 mg/ml, sterile filtered, aliquoted and stored frozen.

8.1 Reduction of Disulfide Bonds in Binding Protein

All reaction steps are typically carried out at 4° C. Where the antibody-binding protein has one or more disulfide bonds, solutions of the binding protein (5-20 mg/mL) in phosphate buffered saline, pH 7.2, are reduced with dithiothreitol (10 mM final) at 37° C. for 30 minutes and separation of low molecular weight agents is achieved by size exclusion chromatography on a Sephadex™ column in PBS containing 1 mM diethylenetriaminepentaacetic acid.

8.2 Determination of Sulfhydryl Content of the Antibody-Binding Protein

The sulfhydryl content of the antibody-binding protein can be determined using 5,5'-dithiobis(2-nitrobenzoic acid) (DTNB) (see Riddles, P. W., Blakeley, R. L., and Zerner, B. Anal. Biochem. 94:75-81 (1979)). To a PBS solution of reduced antibody-binding protein, a Drug-Linker Compound in MeCN is added so that the solution is 20% MeCN/PBS (vol/vol). The amount of Drug-Linker Compound is approximately 10% more than the total number of sulfhydryl groups on a Ligand. After 60 min at 4° C., cysteine is added (20-fold excess over concentration of the Drug-Linker Compound), the solution is concentrated by ultrafiltration, and any low molecular weight agents are removed by gel filtration. The number of Drug-Linker Compounds per antibody is determined by UV/visible spectroscopy using formulas derived from the relative extinction coefficients of the antibody-binding protein and Drug-Linker Compounds. The amount of quenched Drug-Linker Compound is then determined using reverse-phase HPLC. The aggregation state of the antibody-binding protein of the abADC can be determined using size-exclusion HPLC. The Drug-Linker-binding protein conjugates may be used without further purification.

8.3 Reduction of the Inter-Chain Disulfide Bonds of an Antibody-Binding Protein.

To a solution of 24 mg of an antibody binding protein (2.4 mL of 10 mg/mL solution) in suitable buffer is added 300 uL of borate buffer (500 mM sodium borate/500 mM sodium chloride, pH 8.0) followed by 300 uL of dithiothreitol (DTT, 100 mM solution in $H_2O$). The reaction mixture is stirred using a vortex instrument and incubated at 37° C. for 30 minutes. Three size exclusion/desalting columns (e.g., PD-10 desalting columns) are equilibrated with PBS containing 1 mM DTPA (in PBS) and the reduced antibody-binding protein is eluted through the three columns and collected in 4.2 mL PBS/DTPA solution (1.4 mL per column). The reduced antibody is then stored on ice.

8.4 Determination of the Number of Thiols Per Antibody-Binding Protein.

A reference sample of a reduced antibody-binding protein is diluted to about 1:40 (w/w) in PBS, and the UV absorbance of the solution is measured at 280 nm using standard UV spectroscopic methods. Preferably, the amount of antibody-binding protein in the solution is such that the UV absorbance ranges from about 0.13-0.2 AU (absorbance units).

A test sample of a reduced antibody-binding protein from 6.3 above is diluted to about 1:20 with a PBS solution containing about 15 mL DTNB stock solution/mL PBS. A blank sample containing DTNB at the same concentration as the test solution (i.e., 15 µL DTNB stock/mL PBS) is then prepared. The spectrophotometer is referenced at 0 nm with the blank sample, then the absorbance of the test sample is measured at 412 nm.

The molar concentration of the reduced antibody-binding protein is then determined using the formula: [Antibody-binding protein]=$(OD_{280}/2.24e^5)$×dilution factor.

The molar concentration of thiol is then determined using the formula: $[SH]=(OD_{412}/1.415e^4)$×dilution factor.

The [SH]/[Antibody-binding protein] ratio is then calculated. In a preferred embodiment, the [SH]/[Ligand] ratio range is from about 3 to about 4.

8.5 Preparation of Protein A abADC.

Protein A is buffer exchanged with phosphate buffer pH 6.5-7.5 at a concentration of 2-10 mg/mL. A cytotoxic drug, N-hydroxysuccinimide-valine-citrulline-monomethyl auristatin E (NHS-vc-MMAE) is dissolved in dimethyl acetate at a concentration of 10 mM. The solution of NHS-vc-MMAE was added to the buffer exchanged Protein A at a ratio of 4:1 molar ratio. The reaction is performed at room temperature for a time until completed (up to 24 hours). The unreacted NHS-vc-MMAE is removed by size exclusion chromatography (e.g., PD-10). The Protein A-abADC is characterized by UV, Hydrophobic Interaction Chromatography (HIC)-HPLC to determine the number of drug molecules per protein molecule. The average number of drug molecules per Protein A range from 2 to 4.

8.6 Determination of the Number of Drug Molecules Per Protein in an AbADC.

The drug/protein ratio can be calculated by UV absorption, typically, cytotoxic drug has maximum absorption at 252 nm, while protein has peak absorption at 280, by measuring the two absorption peaks at 252 nm and 280 nm and the molar ratio of Drug/protein can be calculated.

Alternatively, HPLC may be used, such as HIC-HPLC to measure the retention time shift and integration area of the unconjugated and conjugated protein.

8.9 Cytotoxic Activity Assay of Protein A-abADC.

Tumor cells are plated on a culture plate at a cell density of 5,000-10,000 cells/well. The cells are incubated in a $CO_2$ incubator overnight. The primary antibody solution is prepared by serially diluting the antibody (200 mM) 2-10 fold in culture medium. Following incubation the medium is removed from the tumor cells and 50-100 uL of antibody solution is added. The abADC solution is prepared by diluting the abADC stock in cell culture medium (e.g., Differentiation Induction Medium, DMI) at a concentration of 200 nM. Approximately 50-100 uL of abADC solution is added to the tumor cells in the culture plate. The cells are incubated in a $CO_2$ incubator for 72 hours at 37° C. Following incubation the unbound antibody and abADC are removed from the tumor cells and 50-100 uL of Celltiter-Glo (Luminescent Cell Viability Assay (Promega, Madison, Wis.) J. Wesierska-Gadek and J. Wojciechowski, CELL NOTES, Issue 6, (2003)) is added to each well and readings are taken within 2 hours.

The $EC_{50}$ (nM) of Trastuzumab (anti-HER2 antibody) bound MMAE was 0.037, the antibody (20 nM and 100 nM concentrations) in combination with Protein A-abADC (20 nM, 40 nM and 100 nM concentrations) ranged from 0.18 to 0.25 and the Protein A-abADC was 214. This data demonstrate that the protein A-abADC was more toxic to these tumor cells than the antibody bound drug or the antibody bound drug in combination with the Protein A-abADC by almost two orders of magnitude.

9.0 Compositions

In other aspects, the present invention provides a first composition comprising an effective amount of an antibody that targets the cells of interest and a second composition comprising an AbADC each provided in a pharmaceutically acceptable carrier or vehicle. For convenience, and for this and the proceeding section only, the antibody that targets the cells of interest and the abADCs of the invention can simply be referred to as compounds of the invention. The compositions are suitable for veterinary or human administration.

The compositions of the present invention can be in any form that allows for the composition to be administered to an animal. For example, the composition can be in the form of a solid, liquid or gas (aerosol). Typical routes of administration include, without limitation, oral, topical, parenteral, sublingual, rectal, vaginal, ocular, and intranasal. Parenteral administration includes subcutaneous injections, intravenous, intramuscular, intrasternal injection or infusion techniques. Preferably, the compositions are administered parenterally. Pharmaceutical compositions of the invention can be formulated so as to allow a Compound of the Invention to be bioavailable upon administration of the composition to an animal. Compositions can take the form of one or more dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal, the particular form of the Compound of the Invention, the manner of administration, and the composition employed.

The pharmaceutically acceptable carrier or vehicle can be particulate, so that the compositions are, for example, in tablet or powder form. The carrier(s) can be liquid, with the compositions being, for example, oral syrup or injectable liquid. In addition, the carrier(s) can be gaseous, so as to provide an aerosol composition useful in inhalatory administration.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is a preferred adjuvant. An injectable composition is preferably sterile.

The amount of the Compound of the Invention that is effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances.

For intravenous administration, the composition may comprise from about 1 to about 250 mg of a Compound of the Invention per kg of the animal's body weight. Preferably, the amount administered will be in the range from about 4 to about 25 mg/kg of body weight of the Compound of the Invention.

Generally, the dosage of Compound of the Invention administered to an animal is typically about 0.1 mg/kg to about 250 mg/kg of the animal's body weight. Preferably, the dosage administered to an animal is between about 0.1 mg/kg and about 20 mg/kg of the animal's body weight, more preferably about 1 mg/kg to about 10 mg/kg of the animal's body weight.

The compounds of the invention or compositions may be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a Compound of the Invention or composition.

In certain embodiments, more than one compound of the invention or composition may be administered to an animal. In a preferred embodiment, the compounds of the invention or compositions are administered intravenously.

In specific embodiments, it can be desirable to administer one or more compounds of the invention or compositions locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue.

Pulmonary administration can also be employed, e.g. by use of an inhaler or nebulizer, and formulation with an aerosolizing agent, or via perfusion in a fluorocarbon or synthetic pulmonary surfactant.

In another embodiment, the compounds of the invention can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

The term "carrier" refers to a diluent, adjuvant or excipient, with which a Compound of the Invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the compounds of the invention or compositions and pharmaceutically acceptable carriers are sterile. Water is a preferred carrier when the compounds of the invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The present compositions, if desired, can also contain minor amounts of wetting or emulsifying agents, or pH buffering agents.

In a preferred embodiment, the compounds of the invention are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form. Where a Compound of the Invention is to be administered by infusion, it can be dispensed, for example, with an infusion bottle containing sterile pharmaceutical grade water or saline. Where the Compound of the Invention is administered by injection, an ampoule of sterile water for injection or saline can be provided so that the ingredients can be mixed prior to administration.

The pharmaceutical compositions can be prepared using methodology well known in the pharmaceutical art. For example, a composition intended to be administered by injection can be prepared by combining a Compound of the Invention with water so as to form a solution. A surfactant can be added to facilitate the formation of a homogeneous solution or suspension. Surfactants are compounds that non-covalently interact with a Compound of the Invention so as to facilitate dissolution or homogeneous suspension of the active compound in the aqueous delivery system.

10.0 Uses of the Compounds and Methods of the Invention

The compounds of the invention are useful for treating cancer, for stem cell therapy in an animal and for discovering therapeutic antibodies.

10.1 Treatment of Cancer

The compounds of the invention are useful for inhibiting the multiplication of a tumor cell or cancer cell. The compounds of the invention can be used accordingly in a variety of settings for the treatment of animal cancers. The abADCs can be used to deliver a Drug or Drugs to a tumor cell or cancer cell. Without being bound by theory, in one embodiment, the first composition provides the targeting antibody that binds the cells of interest. The second composition contains the AbADC that binds the antibody bound to the target cancer cell or tumor cell-associated antigen. The Compound of the Invention can be taken up inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific peptide sequences within the Linker unit are hydrolytically cleaved by one or more tumor-cell or cancer-cell-associated proteases, resulting in release of a Drug or a Drug-Linker Compound. The released Drug or Drug-Linker Compound is then free to migrate in the cytosol and induce cytotoxic activities. In an alternative embodiment, the Drug is cleaved from the Compound of the Invention outside the tumor cell or cancer cell, and the Drug or Drug-Linker Compound subsequently penetrates the cell.

The specificity of the antibody for a particular tumor cell or cancer cell can be important for determining those tumors or cancers that are most effectively treated. For example, a first composition of the compounds of the invention may comprise anti-tumor antibody BR96 that can be useful for treating antigen positive carcinomas including those of the lung, breast, colon, ovaries, and pancreas. compounds of the invention having a first composition comprising an anti-CD30 or anti-CD40 antibody may be useful for treating hematologic malignancies.

Other particular types of cancers that can be treated with compounds of the invention include, but are not limited to, solid tumors, including but not limited to: fibrosarcoma myxosarcoma liposarcoma chondrosarcoma osteogenic sarcoma chordoma angiosarcoma endotheliosarcoma lymphangiosarcoma lymphangioendotheliosarcoma synovioma mesothelioma Ewing's tumor leiomyosarcoma rhabdomyosarcoma colon cancer colorectal cancer kidney cancer pancreatic cancer bone cancer breast cancer ovarian cancer prostate cancer esophogeal cancer stomach cancer oral cancer nasal cancer throat cancer squamous cell carcinoma basal cell carcinoma adenocarcinoma sweat gland carcinoma sebaceous gland carcinoma papillary carcinoma papillary adenocarcinomas cystadenocarcinoma medullary carcinoma bronchogenic carcinoma renal cell carcinoma hepatoma bile duct carcinoma choriocarcinoma seminoma embryonal carcinoma Wilms' tumor cervical cancer uterine cancer testicular cancer small cell lung carcinoma bladder carcinoma lung cancer epithelial carcinoma glioma glioblastoma multiforme astrocytoma medulloblastoma craniopharyngioma ependymoma pinealoma hemangioblastoma acoustic neuroma oligodendroglioma meningioma skin cancer melanoma neuroblastoma retinoblastoma blood-borne cancers, including but not limited to: acute lymphoblastic leukemia "ALL" acute lymphoblastic B-cell leukemia acute lymphoblastic T-cell leukemia acute myeloblastic leukemia "AML" acute promyelocytic leukemia "APL" acute monoblastic leukemia acute erythroleukemic leukemia acute megakaryoblastic leukemia acute myelomonocytic leukemia acute nonlymphocytic leukemia acute undifferentiated leukemia chronic myelocytic leukemia "CML" chronic lymphocytic leukemia "CLL" hairy cell leukemia multiple myeloma acute and chronic leukemias: lymphoblastic myelogenous lymphocytic myelocytic leukemias Lymphomas: Hodgkin's disease non-Hodgkin's Lymphoma Multiple myeloma Waldenstrom's macroglobulinemia Heavy chain disease Polycythemia vera

10.2 Stem Cell Therapy

Cardiomyocytes formed from iPS-derived cells are treated with anti-stem cell surface marker such as CD11, CD117 antibody for 1 hour at 37° C. The anti-antibody drug conjugate is added to these cardiomyocytes and incubated in a $CO_2$ incubator for three days. iPS-derived cells are removed by washing the tissue.

10.3 Therapeutic Antibody Discovery

To screen a panel of antibodies as candidates for anti-antibody drug conjugates, a 96 well plate is coated with 5,000 cancer cells/well, antibodies to be screened are added to the wells at a desired concentration, an equivalent concentration of antibody binding protein is then added. Incubate the cancer cell are incubated in $CO_2$ incubator for 72 hours. The viability of cancer cells are measured by a cell viability assay such as TiterGlow assay (Wesierska-Gadek and Wojciechoski, Cell Notes, Issue 6, (2003)). The antibodies that show greater than or equal to 30% cell killing are considered potential candidates for the preparation of ADCs.

The methods and compounds of the invention provide specific cancer or stem cell targeting, thus reducing general toxicity of these compounds. The Linker units stabilize the compounds of the invention in blood, yet are cleavable by tumor-specific proteases within the cell, liberating a Drug. In addition, the compounds of the invention may be used in assays to screen antibodies to identify those that will have the greatest efficacy as antibody drug conjugates.

What is claimed is:

1. A composition consisting of one or more therapeutic drugs covalently bound to an antibody-binding agent, wherein said antibody-binding agent does not directly bind to cancer or stem cells and wherein said antibody-binding agent is protein A, protein G, protein A/G or protein L.

2. A composition according to claim 1, wherein said therapeutic drug is selected from the group consisting of a microtubulin binding agent, a DNA interchelating agent, an antineoplastic agent and a DNA damaging agent.

3. A composition according to claim 1, wherein said composition is used to treat cancer and wherein said cancer cells are selected from the group consisting of A431, D549 and SKBR3.

* * * * *